US00PP16359P3

(12) United States Plant Patent
Hasegawa

(10) Patent No.: US PP16,359 P3
(45) Date of Patent: Mar. 21, 2006

(54) CARNATION PLANT CALLED 'CFPC BELEZA'

(50) Latin Name: *Dianthus caryophyllus*
Varietal Denomination: CFPC Beleza

(76) Inventor: Oscar T. Hasegawa, 1721 Burlington Dr., Salinas, CA (US) 93906

( * ) Notice: Subject to any disclaimer, the term of this patent is extended or adjusted under 35 U.S.C. 154(b) by 144 days.

(21) Appl. No.: 10/837,429

(22) Filed: Apr. 30, 2004

(65) Prior Publication Data

US 2005/0246809 P1 Nov. 3, 2005

(51) Int. Cl.
*A01H 5/00* (2006.01)

(52) U.S. Cl. ..... Plt./273

(58) Field of Classification Search ..... Plt./273
See application file for complete search history.

*Primary Examiner*—Anne Marie Grunberg
(74) *Attorney, Agent, or Firm*—Christie, Parker & Hale, LLP

(57) ABSTRACT

A new and distinct variety of carnation plant characterized by a distinctive bright red flower color.

1 Drawing Sheet

Latin name of genus and species: The present invention relates to a new and distinct variety of hybrid *Dianthus caryophyllus*. The varietal denominator of the new variety is 'CFPC Beleza'.

BACKGROUND OF THE INVENTION

The present invention relates to a new and distinct variety of carnation plant, named 'CFPC Beleza', which is a sport of the selection 990246 (non-patented), a commercially available, red colored carnation of the CFPC Adorable family. The female parent of 990246 is identified as 'CFPC selena' (U.S. Plant Pat. No. 11,899), color crimson; the male parent in an unknown seedling. The primary objective of the controlled breeding program was to extend the color range of the CFPC Romance series to include a bright red flower. The closest commercial cultivar in color to the new cultivar of which I am aware is the carnation 'CFPC Tiara' (U.S. Plant Pat. No. 14,797). Tiara is a shorter cultivar in the Adorable series.

SUMMARY OF THE INVENTION

Among the novel characteristics possessed by the new variety which distinguishes it is a distinctive bright red flower color, which retains its color without fading. When grown in 4½ inch pots in Salinas, Calif., plant diameter averages about 6½ inches. Pinched plants are about 7½ to 7¾ inches tall and flowers are about 1¾ inches average diameter with a crown higher than about ⅝ inches. Foliage is about 4 inches long and about 5/16 inches wide.

Asexual reproduction and flowering of this new cultivar by side shoot cuttings as performed in Salinas, Calif., shows that the foregoing and other distinguishing characteristics come true to form and are established and transmitted through succeeding propagations.

COMPARISON TO PARENTS

'CFPC Beleza' is characterized by a distinctive bright red color flower, which retains its color without fading. The flower is brighter than that of 990246, a red colored carnation of the CFPC Adorable family, of which 'CFPC Beleza' is a sport. The female parent of 990246, CPFC Selena, has a crimson flower; the male parent of 990246 is unknown.

BRIEF DESCRIPTION OF ILLUSTRATIONS

The accompanying photographic illustration shows a typical specimen of the new variety in color as nearly true as it is reasonably possible to make in a color illustration of this character.

DESCRIPTION OF THE NEW VARIETY

Referring now specifically to the new and distinct variety of carnation plant the following is a detailed description of 'CFPC Beleza', approximate age 121 days, with color description where indicated by reference to The Royal Horticultural Society Colour Chart, except where common terms of color definition are employed.

The new variety of carnation plant as herein disclosed may vary in slight detail due to climatic, soil and cultural conditions under which the variety may be grown, the present description being of the variety as grown at Salinas, Calif.

The new variety is a greenhouse-type plant, suitable for production as a pot spray.

Plant:

*Height.*—About 7½–7¾ inches tall.
*Form.*—Herbaceous.
*Growing habit.*—Semi-upright.
*Blooming habit.*—As a spray when grown in a pot; blooming time, approximately 110 days.
*Shelf life.*—Approximately 21 days in bloom.
*Blooming season.*—Year round.
*Rooting time.*—About 18 days.
*Breaking action.*—Good.
*Mutation prone.*—No.
*Disease resistance.*—Resistant to *Fusarium oxysporum* and *Fusarium graminearum.*

Foliage:
*Color.*—Upper side: near 137A; lower side: near 139B.
*Size.*—Length: about 4 inches; width: about 5/16 inches.
*Quantity.*—Numerous.
*Shape.*—Lanceloate.
*Texture.*—Smooth.
*Ribs.*—Central keel.
*Arrangement.*—Bilateral along stem.
*Stem color.*—Near 138D.

Bud:
*Shape.*—Ovoid.
*Color.*—Near 137C.
*Size.*—Length: about 1 inch; diameter: about 7/16 inches.

Calyx:
*No. of lobes* (*sepals*).—Five.
*Size.*—Length: about ¼ inches; width: about 3/16 inches.
*Color.*—Outside: near 139C; inside: near 138D.

Bloom:
*Shape.*—Rounded.
*Size.*—Diameter (average): about 1¾ inches; depth (average): about ⅝ inches.
*Borne.*—As a spray.
*Color.*—General tonality: red; Upper side: near 46B; Lower side: near 46D; Center: near 45B; Outer petals: near 46B; Base: near 147D.
*Permanence.*—Dry up on receptacle.
*Keeping quality.*—Good.
*Fragrance.*—Slight.

Petalage:
*Number.*—Twenty six.
*Outer petals.*—Length: about 1 11/16 inches; Width: about 11/16 inches.
*Central petals.*—Length: about 1½ inches; Width: about ¼ inches.
*Texture.*—Smooth.
*Appearance.*—Shiny.
*Form.*—Fan-shaped.

Reproductive organs:
*Stamen.*—None (male sterile).
*Anthers.*—None.
*Filaments.*—None.
*Pistil.*—Length: 1⅜ inches; Number: one (trilobed). Color: White (whiter than 155D).
*Stigma.*—Number: 3; Color: White (whiter than 155D).
*Fertility.*—Male: sterile.
*Ovary.*—Shape: conical; Color: base near 145D, body near 145A, apex near 145A.
*Size.*—Length: about 5/16 inches; Width: about ¼ inches.

I claim:

1. A new and distinct variety of carnation plant identified as 'CFPC Beleza', substantially as shown and described.

* * * * *

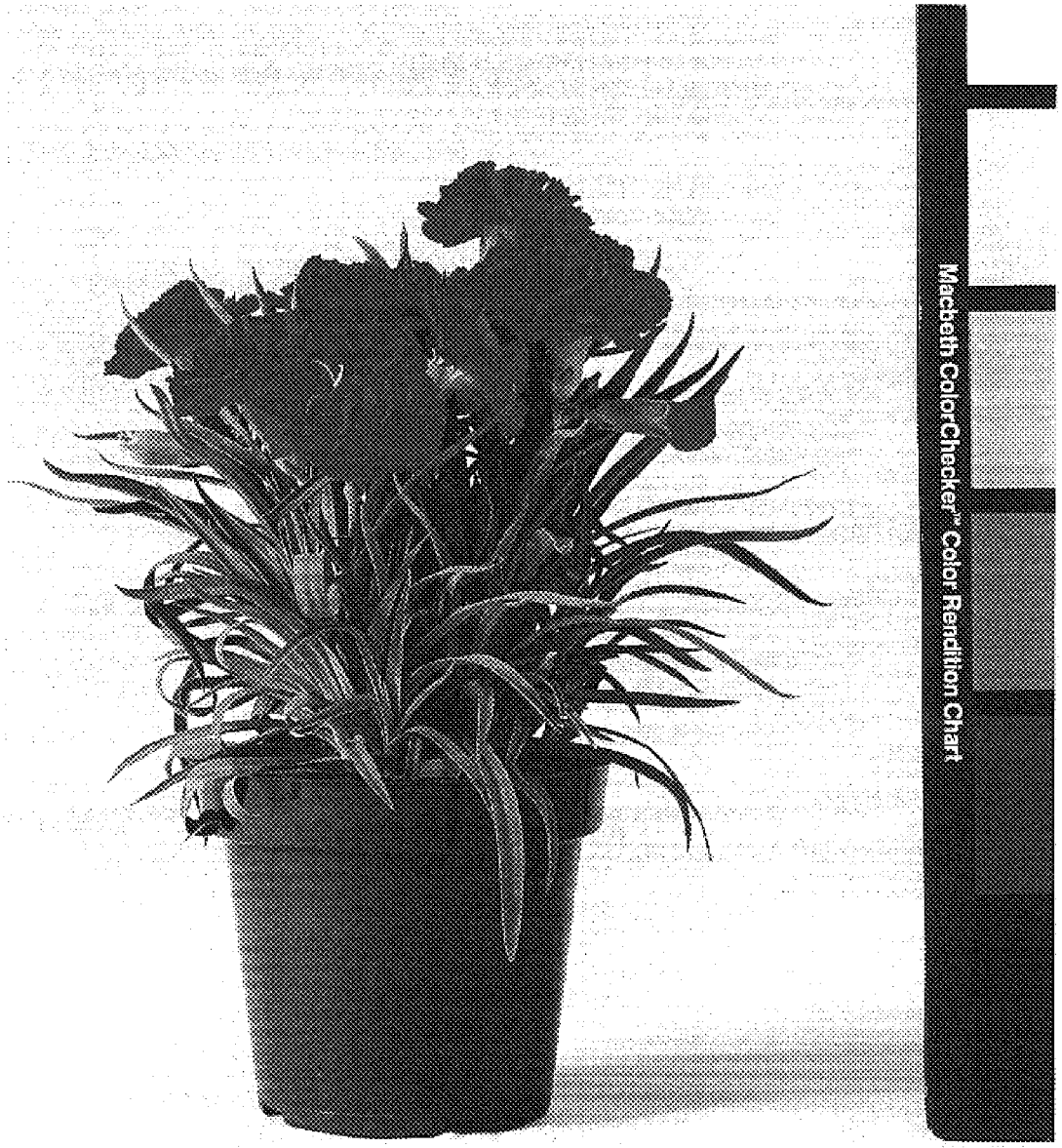
Macbeth ColorChecker™ Color Rendition Chart